US011278300B2

(12) United States Patent
Bahmanyar et al.

(10) Patent No.: US 11,278,300 B2
(45) Date of Patent: Mar. 22, 2022

(54) ANGIOPLASTY OF CALCIFIED ARTERIES

(71) Applicants: IMPERIAL COLLEGE INNOVATIONS LIMITED, London (GB); UNIVERSITY OF LEICESTER, Leicester (GB)

(72) Inventors: Mohammad Reza Bahmanyar, London (GB); David Adlam, Leicester (GB)

(73) Assignees: UNIVERSITY OF LEICESTER, Leicester (GB); IMPERIAL COLLEGE INNOVATIONS LIMITED, London (GB)

( * ) Notice: Subject to any disclaimer, the term of this patent is extended or adjusted under 35 U.S.C. 154(b) by 230 days.

(21) Appl. No.: 16/089,755

(22) PCT Filed: Mar. 29, 2017

(86) PCT No.: PCT/GB2017/050877
§ 371 (c)(1),
(2) Date: Sep. 28, 2018

(87) PCT Pub. No.: WO2017/168145
PCT Pub. Date: Oct. 5, 2017

(65) Prior Publication Data
US 2020/0306512 A1    Oct. 1, 2020

(30) Foreign Application Priority Data
Mar. 29, 2016    (GB) ..................... 1605255

(51) Int. Cl.
*A61B 17/22*    (2006.01)
(52) U.S. Cl.
CPC .... *A61B 17/22* (2013.01); *A61B 2017/22001* (2013.01)

(58) Field of Classification Search
CPC ........... A61M 25/104; A61M 25/1018; A61M 25/10181; A61M 25/10182;
(Continued)

(56) References Cited

U.S. PATENT DOCUMENTS 4,446,867 A * 5/1984 Leveen ............ A61B 17/22012
128/DIG. 12
5,413,581 A * 5/1995 Goy ....................... A61M 25/01
606/194

(Continued)

FOREIGN PATENT DOCUMENTS

EP    0083870 A1    7/1983
EP    0744163 A1    11/1996
(Continued)

OTHER PUBLICATIONS

Watson et al., Invasive Cardiology: A Manual for Cath Lab Personnel, Jones & Bartlett Learning; 3 edition, (2011).
(Continued)

*Primary Examiner* — Melanie R Tyson
(74) *Attorney, Agent, or Firm* — Marshall, Gerstein & Borun LLP

(57) ABSTRACT

A medical device for assisting the break-up, disruption or disintegration of calcified or other hardened material within vessels of the human or animal body which material otherwise prevents or inhibits stenting procedures or passage of guidewires, catheters and other devices through the vessels. The device includes a catheter having a lumen extending between a distal end and a proximal end of the catheter and a displaceable element at the distal end of the catheter configured for axial and/or radial displacement relative to the catheter when driven by pressure fluctuations within the lumen. A pressure pump is coupled to a proximal end of the catheter and is configured for application of a baseline pressure to the catheter lumen. A pressure modulation source
(Continued)

is also coupled to the proximal end of the catheter, configured to modulate the baseline pressure in the catheter lumen with one or more pressure impulses, and preferably with a series of pressure pulses.

13 Claims, 5 Drawing Sheets

(58) Field of Classification Search
CPC ...... A61M 25/10183; A61M 25/10184; A61M 25/10187; A61M 25/1086; A61M 2025/102; A61M 2025/1022; A61M 2025/109; A61M 2205/3351; A61B 17/22; A61B 17/22004; A61B 17/22012; A61B 17/22032; A61B 2017/22001; A61B 2017/22005
See application file for complete search history.

(56) References Cited

U.S. PATENT DOCUMENTS

| | | | |
|---|---|---|---|
| 5,486,192 A | | 1/1996 | Walinsky et al. |
| 5,527,336 A | * | 6/1996 | Rosenbluth ............ A61F 2/958 600/116 |
| 5,722,979 A | | 3/1998 | Kusleika |
| 5,885,244 A | | 3/1999 | Leone et al. |
| 6,626,861 B1 | | 9/2003 | Hart et al. |
| 2009/0171278 A1 | * | 7/2009 | Hirszowicz ...... A61B 17/22012 604/97.01 |
| 2009/0312768 A1 | * | 12/2009 | Hawkins ............ A61B 17/2202 606/128 |
| 2010/0121270 A1 | * | 5/2010 | Gunday ................ A61M 1/008 604/98.01 |
| 2012/0265283 A1 | | 10/2012 | Mack et al. |
| 2015/0141917 A1 | * | 5/2015 | Tilson ................... A61F 2/958 604/103.07 |

FOREIGN PATENT DOCUMENTS

| | | |
|---|---|---|
| FR | 1278965 A | 12/1961 |
| WO | WO-95/31245 A1 | 11/1995 |
| WO | WO-00/38776 A1 | 7/2000 |
| WO | WO-2011/142758 A1 | 11/2011 |
| WO | WO-2015/087086 A1 | 6/2015 |

OTHER PUBLICATIONS

Lanzer et al., "Medial vascular calcification revisited: review and perspectives," *European Heart Journal,* (2014).
Ludman, Peter F., "BCIS Audit Returns Adult Interventional Procedures," Cambridge 4th (2013).
Cockburn et al., "Contemporary clinical outcomes of patients treated with or without rotational coronary atherectomy—An alaysis of the UK central cardiac audit database," International Journal of Cardiology (2014).
Genereux et al., "Ischemic Outcomes After Coronary Intervention of Calcified Vessels in Acute Coronary Syndromes," Journal of the American College of Cardiology, vol. 63 (2014).
Mattesini et al., "ABSORB Biodegradable Stents Versus Second-Generation Metal Stents," JACC: Cardiovascular Interventions, vol. 7 (2014).
McClain et al., "Optimizing ShockWave Lithotripsy: A Comprehensive Review," Reviews in Urology, vol. 15 (2013).
International Search Report issued in PCT/GB2017/050877 dated Sep. 15, 2017.
Written Opinion issued in PCT/GB2017/050877 dated Sep. 15, 2017.
Combined Search and Examination Report issued in Great Britain Patent Application No. 1605255.7 dated Sep. 1, 2016.

* cited by examiner

ANGIOPLASTY OF CALCIFIED ARTERIES

TECHNOLOGICAL FIELD

The present invention relates to methods and apparatus suitable for the disruption and/or disintegration of material that has built up on arterial walls, particularly though not exclusively for use during angioplasty procedures.

BACKGROUND

Coronary artery disease is a common clinical condition associated with high morbidity and mortality in developed countries. It is often treated by percutaneous coronary intervention (PCI), including Plain Old Balloon Angioplasty (POBA) as well as stenting and atherectomy. Coronary calcification is an inherent element of atherosclerotic coronary disease and presents significant challenges to PCI procedures because vascular mural calcification can prevent effective coronary dilation, e.g. by balloon angioplasty, potentially risking incomplete expansion of coronary stents, a well-established risk factor for post PCI major adverse cardiovascular events (MACE) including stent thrombosis and in stent restenosis.

Coronary calcification restricts balloon inflation and increases procedural complexity and the risk of complications including coronary perforation or dissection. Adequate lesion dilation is critical for long term outcomes, especially with next-generation bioabsorbable stents with reduced radial strength. Some calcified lesions are non-dilatable by conventional PCI techniques. Patients with extensive coronary calcium are frequently referred for surgical revascularisation. This problem is increasing as the population ages, because calcification is associated with age and older co-morbid patients are less suited to surgery.

Existing methods used to address the challenges of calcification include so-called 'cutting' balloons (balloons fitted with blades) and rotational atherectomy where a rotating diamond coated burr is introduced and used to disrupt the calcification. Such scored 'cutting' balloons or rotational atherectomy devices involve procedural techniques which require significant operator experience and are often associated with increased periprocedural complication rates.

It would be advantageous to provide alternative techniques to assist in the break-up, disruption or disintegration of calcified material or other hardened material within vessels of the human or animal body which material otherwise prevents or inhibits stenting procedures or passage of guidewires, catheters and other devices through the vessels.

SUMMARY OF THE DISCLOSURE

According to one aspect, the present invention provides a medical device comprising:
  a catheter having a lumen extending between a distal end and a proximal end of the catheter;
  a displaceable element at the distal end of the catheter configured for axial and/or radial displacement relative to the catheter when driven by pressure fluctuations within the lumen;
    a pressure pump coupled to a proximal end of the catheter and configured for application of a baseline pressure to the catheter lumen;
  a pressure modulation source, coupled to the proximal end of the catheter, configured to modulate the baseline pressure in the catheter lumen with one or more pressure impulses.

The catheter may comprise a balloon catheter and the displaceable element may comprise an inflatable balloon; wherein the pressure pump is configured for inflation of the balloon by the application of the baseline pressure to the balloon via the catheter lumen; and the pressure modulation source is configured to modulate the baseline pressure at the balloon with the one or more pressure impulses.

The pressure modulation source may be configured to modulate the baseline pressure with a series of pressure pulses. The pressure modulation source may comprise a diaphragm displaceable by an electromagnetic actuator. The electromagnetic actuator may comprise a plunger or a cam driven by a motor. The motor may comprise a stepper motor capable of delivering a single impulse to the diaphragm. The pressure modulation source may comprise an acoustic transducer.

The balloon may comprise an outer surface layer or structure configured to localise outward force of the balloon generated by the pressure impulses to only a portion of the balloon external surface. The balloon outer surface structure may comprise a sleeve having a plurality of axially extending elements which are radially displaceable by balloon expansion. The balloon outer surface structure may comprise a mesh having one or more weights disposed on the mesh. The balloon outer surface structure may comprise an end surface which is axially displaceable by the one or more pressure impulses.

The pressure modulation source may be configured to modulate the pressure with a waveform having a frequency greater than 5 Hz, greater than 10 Hz or greater than 100 Hz. The pressure modulation source may be configured to vary a frequency of modulation of the pressure to a resonant frequency of the balloon and any outer surface structure of the balloon, or to a resonant frequency of the system in which the balloon catheter is deployed.

According to another aspect, the invention provides a balloon catheter comprising:
  a catheter having a proximal end and a distal end;
  an inflatable balloon disposed at the distal end of the catheter;
  a flexible outer structure disposed over the balloon configured to localise outward force of the balloon, when inflated, to only a portion of the balloon external surface.

The flexible outer structure may comprise a sleeve having a plurality of axially extending elements which are radially displaceable by balloon expansion. The balloon outer surface structure may comprise a mesh sleeve having one or more weights disposed on the mesh.

According to another aspect, the invention provides a catheter pump for pressurizing a lumen of a catheter, the pump comprising:
  a pressure pump having an outlet for coupling, in use, to a proximal end of a catheter and configured for pressurization of the catheter by the application of a baseline pressure to the outlet;
  a pressure modulation source, coupled to the outlet, configured to modulate the baseline pressure at the outlet with one or more pressure impulses.

The pressure modulation source may be configured to modulate the baseline pressure with a series of pressure pulses. The pressure modulation source may be configured to modulate the baseline pressure with a waveform having a frequency greater than 5 Hz, greater than 10 Hz or greater than 100 Hz. The pressure modulation source may comprise a diaphragm displaceable by an electromagnetic actuator. The electromagnetic actuator may comprise a plunger or a cam driven by a motor. The motor may comprise a stepper motor capable of delivering a single impulse to the diaphragm. The pressure modulation source may comprise an acoustic transducer. The pressure modulation source may be configured to vary a frequency of modulation to establish a resonant frequency of the system to which it is attached.

According to another aspect, the invention provides a method of delivery of an endoluminal device to a vessel comprising:
- inserting a balloon catheter into the vessel;
- inflating the balloon, with a pressure pump, to a baseline pressure facilitating engagement of the balloon with deposited material on an internal wall of the vessel;
- applying a dynamic pressure modulation to the baseline pressure in the balloon so as to deliver pressure pulses to the surface of the balloon and thereby to the deposited material, to cause break-up, disruption or disintegration of deposited material on the internal wall of the vessel.

The pressure pulses at the surface of the balloon may be delivered to the deposited material via an outer structural element disposed over the balloon surface.

According to another aspect, the invention provides a method of breaking up, disrupting or disintegrating calcified or other hardened material within vessels of the human or animal body comprising transmitting percussive forces along a catheter lumen by pressure modulation of a baseline pressure of a fluid within a lumen of the catheter.

BRIEF DESCRIPTION OF THE FIGURES

Embodiments of the present invention will now be described by way of example and with reference to the accompanying drawings in which:

FIG. 6 shows schematic cross-sectional views of an artery having calcified deposits inhibiting stenting procedures or the passage of guidewires, catheters and other devices through the vessels, in which

DETAILED DESCRIPTION

A challenge with vascular mural calcification is that it can be hard and brittle. This combination can create particular difficulties during percutaneous angioplasty. To overcome hardness may require the use of very high pressures during balloon inflation, whilst brittleness means that instead of plastic deformation occurring under the application of increasing pressure, a sudden failure may occur. It is this hard and brittle behaviour which makes traditional balloon dilation of calcified vessels difficult or risky (e.g. potentially leading to dissection or perforation as a result of sudden calcium fracturing at high inflation pressures).

However, it is the hardness and brittleness of calcium that is exploited in this invention. Lack of plastic deformation in calcium results in fracture upon application of a large enough force. Mechanical impacts result in production of large forces over the short impulse time during which the energy is transferred from one object to the other. This principle is used to disrupt vascular mural calcification by local application of a mechanical impulse of sufficient energy. Incompressible fluids can transmit energy very efficiently. An incompressible fluid such as a saline solution within a rigid tube can therefore be used as an energy transmission line.

Figure 1:
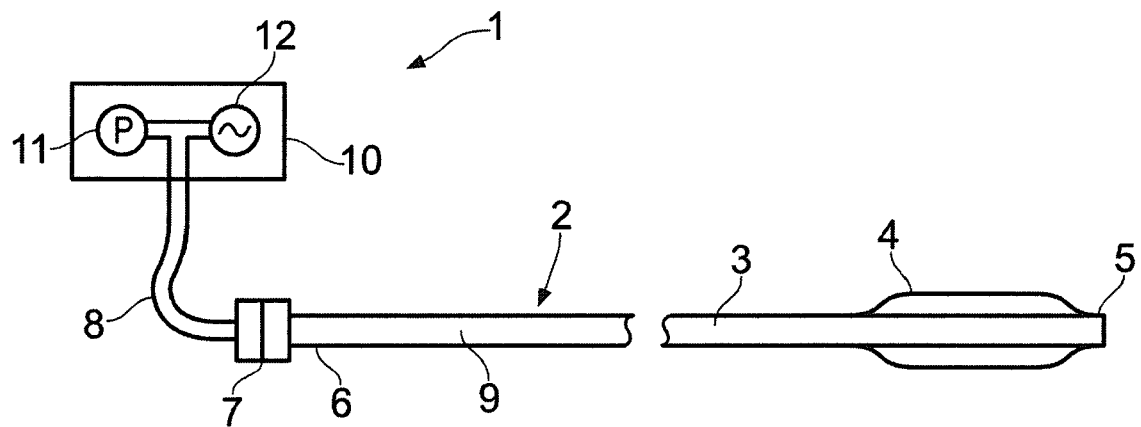
FIG. 1 shows a schematic diagram of a balloon catheter and a pressure delivery mechanism for balloon inflation.

FIG. 1 shows a medical device 1 comprising a balloon catheter 2 comprising a catheter 3 having an inflatable balloon 4 at a distal end 5 of the catheter 3. At the proximal end 6 of the catheter 3 is a connector 7 for connection of the balloon catheter 2 to a pressure control apparatus 10 via a suitable conduit 8. The pressure control apparatus 10 includes a pump 11 of any suitable type for inflation of the balloon 4 by pressurization with, for example, a saline fluid via the conduit 8 and a lumen 9 within the catheter 3. The balloon inflation device may comprise a manual pump such as a piston and screw drive mechanism or an electronically controlled pump, for example. The balloon inflation device may be any suitable type of pump or pressurization device capable of providing a baseline pressurization to the conduit 8 and thereby to the catheter lumen 9 and thereby to the balloon 4, which is sufficient to inflate the balloon to a normal operating pressure for radial expansion of the balloon to engage the walls of a vessel in which the distal end 5 of the catheter 3 is inserted.

The pressure control apparatus 10 further includes a pressure modulation source 12 which is coupled to the pump 11, or to a pressurization chamber leading from the pump to the conduit 8. The pressure modulation source 12 may be any suitable type of device which can impart one or more pressure impulses to the conduit 8 and thereby to the catheter lumen 9 and thereby to the balloon 4. The pressure impulses are of short duration, e.g. typically of pulse width of the order of 0.1 second or less, and more preferably in the range of 0.01 second or less. The pressure modulation source 12 is preferably configured to deliver a series of such pressure impulses, e.g. at a frequency of 5 Hz or more, 10 Hz or more, and more preferably at a frequency of 100 Hz or more. The pressure impulses may encompass audio frequencies or ultrasonic frequencies. The pressure modulation source 12 may be configured to deliver a series of pressure impulses at a frequency of up to 100 Hz, up to 1 kHz, or up to 10 kHz, or higher. The pressure impulses may generally comprise a time varying pressure superimposed on the baseline pressure provided by the pump 11 and may be of any suitable waveform, including, sinusoidal wave, square wave, triangular wave, sawtooth wave, repeated delta function or transient spike etc.

The pressure impulses are transmitted by the fluid medium, such as saline fluid, in the lumen 9 to the inflated surface of the balloon 4. Such pressure impulses delivered via a relatively incompressible fluid such as water/saline in the lumen can produce a great amount of force over a short time interval as shock waves travel along the fluid medium. Delivery of such pressure impulses by incompressible fluids is a highly efficient and effective way of transmitting power almost instantly, and with highly controlled amounts of energy. The energy can be carefully and precisely controlled by managing one or more of: the amplitude of the pressure modulation, the width of the modulation pulses; the shape of the modulation pulses; and the frequency of the modulation pulses, for example. Control of other parameters may be possible.

Figure 6A:
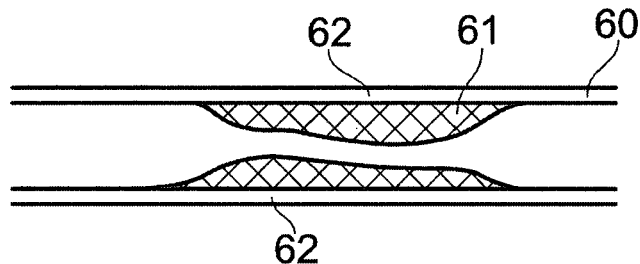
FIG. 6a represents a state of mural calcification forming a partial occlusion.

In conventional procedures, a balloon such as balloon 4 may be inflated to a particular pressure to radially expand the balloon sufficiently to engage the walls of the vessel (e.g. artery) in which it is inserted. With reference to FIG. 6a, where the vessel 60 (e.g. artery) includes fatty deposits, plaques and/or calcification 61 on the walls of the vessel, a balloon may be inflated to compress, expand and/or break these deposits. However, such conventional procedures are not always successful or may involve high risk because the inflation of the balloon may not be capable of breaking hardened calcification and/or because the vessel wall 62 may distend to undesirable extent without actually enabling the break-up of the deposits 61. Sudden perforation of an artery or bursting of a balloon can be a potential undesirable outcome.

However, by using the high frequency impulses provided by the pressure modulation source 12 and modulated onto the baseline pressure that inflated the balloon 3, percussive shock forces may be applied to the deposits 61, greatly increasing the likelihood of break-up, disruption or disintegration of the deposits. Various techniques are known in the art for capturing or otherwise dealing with deposits that have been dislodged or detached, such as during rotational atherectomy as referred to earlier. Such techniques can also be applied here and will not be described further.

Thus, the medical device 1 as described in connection with FIG. 1 enables localised endovascular therapy at a controlled depth and energy for disrupting the vascular calcium to facilitate subsequent PCI. The medical device 1 can be based on existing low-profile angioplasty balloon devices which can be delivered as an over-the-wire microcatheter into even challenging coronary anatomies.

Initially, a moderate baseline pressure may be established to inflate the balloon to the point where it is restricted by the hard calcification. This moderate baseline pressure is preferably within the safe range typically used in balloon angioplasty and provides a relatively incompressible medium ready to receive the pressure impulses. The impact energy provided by the pressure impulses via the conduit 8 and catheter lumen 9 is delivered very locally, directly to the hard and brittle calcification, resulting in calcium micro-fracturing in situ within the vessel wall and without significant displacement. Intramural vascular calcification is embedded within the atherosclerotic plaque and thus embolization after micro-fracturing is unlikely. The local disruption of calcium then enables subsequent low pressure arterial dilation with conventional angioplasty techniques.

Various improvements and enhancements can be made to the apparatus as described in connection with FIG. 1.

In one type of modification, it is recognised that the balloon 4 can be further modified to deliver the percussive pressure impulses to the deposits 61 in the vessel 60 in a more focussed way. The force delivered by the pressure impulses to the balloon surface may be distributed across the balloon surface. In some circumstances, it may be desirable to focus the energy of the pressure impulses into smaller areas so as to increase the force applied to localised areas of the deposits 61. Particularly for hardened, e.g. calcified, deposits that are difficult to break but are hardened (e.g. of low compliance), an improvement in performance of the medical device 1 may be achieved by providing the balloon 4 with an outer surface structure that is particularly configured to localise outward force of the balloon as generated by the pressure impulses to only a portion of the balloon surface. The portion of the balloon surface corresponding to the localised force may comprise a set of portions of the balloon surface.

In one arrangement, the balloon surface itself could be modified by a suitable layer of harder, less elastic or less plastic material at selected positions on the balloon surface. Such harder regions could comprise ribs or nodules in or on the balloon surface, e.g. as an outer surface layer of the balloon or an additional outer surface layer.

In another arrangement, the balloon is provided with an additional structure which can be positioned over the balloon before the catheter is introduced into the vessel undergoing treatment. The additional structure may take the form of a mesh sleeve as illustrated in FIGS. 2 and 3.

Figure 2:
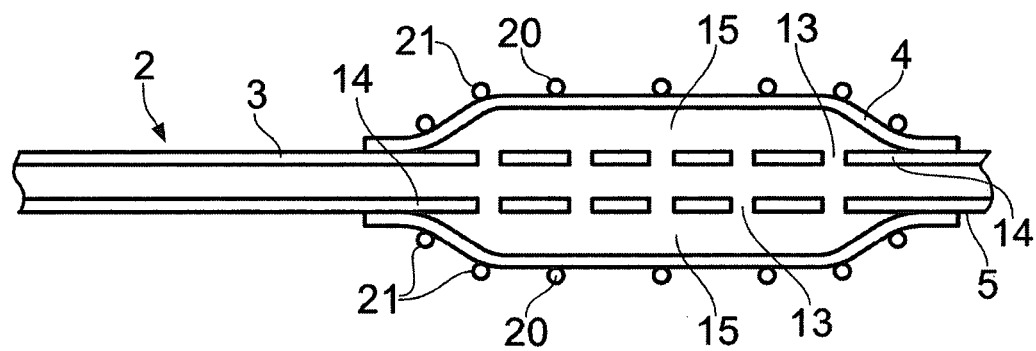
FIG. 2 shows a schematic cross-sectional diagram of a part of a balloon catheter having an outer structure configured to provide localised, radially outward force on inflation of the balloon.
Figure 3:
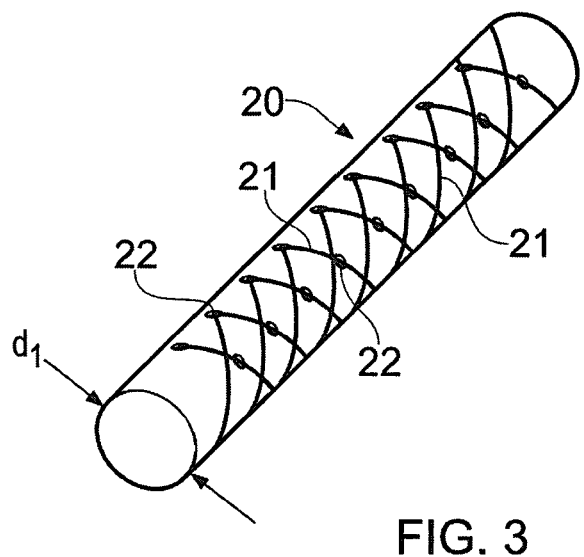
FIG. 3 shows a schematic perspective view of the balloon outer structure of FIG. 2.

With reference to FIG. 2, the distal end 5 of the catheter 3 has the balloon 4 disposed over a series of holes 13 in the wall 14 of catheter lumen 9 for delivery of the pressurization medium such as saline to the internal volume 15 of the balloon 4. (For completeness, it is noted that the lumen 9 may be an outer lumen of the catheter 3, with the catheter having an inner lumen (not shown) through which a guidewire may pass in known manner, so that the balloon catheter 2 can be introduced into a vessel 60 over a guidewire (also not shown) using well established techniques. For clarity, these features are omitted from the drawings.) The balloon 4 further includes a mesh sleeve 20 comprising a network of wires 21 or other link members more easily seen in the perspective view of FIG. 3. Preferably, the mesh sleeve 20 is microfabricated from metal or other relatively hard material so that the individual wires 21 or other link members are themselves relatively incompressible, though the overall mesh itself is quite flexible. An example would be a Nitinol mesh or other superelastic alloy. The mesh sleeve 20 is preferably configured such that it can be compressed radially so that it has a low profile, e.g. a diameter commensurate with the uninflated balloon 4, but will expand radially with the balloon 4 when the balloon is inflated.

In this way, the mesh sleeve 20 may have little effect on the diameter of balloon catheter 2 used in the vessel 60 during delivery, but will expand with the balloon when the balloon is inflated in situ. Each wire 21 or other link member may provide a localised hard surface which is used as a hammer surface against the deposits 61 when the balloon surface is displaced by the pressure impulses from the pressure modulation source 12.

More preferably, the force from the pressure impulses may be focussed to even more localised regions by the formation of small weights or nodules 22 affixed to or formed on the wires 21 or other link members. These weights are preferably dispersed over at least parts of the sleeve 20 so that they provide small points of hard surface to serve as hammer surfaces against the deposits 61 when the balloon surface is displaced by pressure impulses from the pressure modulation source 12. In this way, the forces provided by the pressure impulses from pressure modulation source 12 may be even more highly localised. The weights or nodules can be generally added to the sleeve by welding or electroforming.

In use, the inflatable balloon 4 is inflated with the pressurised fluid at a desired pressure so that the balloon and mesh with or without weights is in contact with the deposits 61. The pump 11 maintains a static pressure on which is superimposed a dynamic high frequency component by the pressure modulation source 12. The liquid filled catheter lumen 9 acts as the energy transmission medium. The pressure pulse(s) are generated within the relatively incompressible fluid-filled space, passing into the vessel wall at sufficient energy to disrupt local mural calcification but with controlled depth penetration, thereby avoiding the potential for non-target injury and minimal potential for localised vacuolation within the coronary blood flow, which may be transiently excluded by balloon inflation.

This approach may also have a clinical advantage of having similarity of deployment with existing technologies used for PCI procedures, such that it can potentially be readily adopted by interventional cardiologists having skills in balloon catheter stent deployment.

In some preliminary trials, a conventional dilation catheter 2 has been used with a mesh 20 suitable to produce the required impact forces. A simple structure fitted with weights 22 was fabricated from 100 micron diameter nitinol wire and attached to a laser cut nitinol spring that can easily slide on a 400 micron (guide wire). This structure was fabricated to investigate the way a weighted mesh can potentially be used to modify a standard balloon catheter to fit the purpose. Testing the wired structure on the balloon suggests that a precision microfabricated mesh sleeve 20 comprising tungsten weights may be made to meet the size and impact requirements.

Another form of mesh sleeve 20 that may be considered can be fabricated from a cylindrical metal element into which a plurality of holes, slots or slits may be laser etched thereby defining a mesh framework without the use of discrete wires. The cylindrical metal element is formed from thin sheet metal (e.g. of a thickness around 100 microns) so that the mesh can be of similar thickness and flexibility to that formed by the wires 21 as described above in connection with FIGS. 2 and 3. Such a cylindrical etched element can also be adapted to include weights 22 if desired, e.g. by welding. Other techniques could be used to microfabricate a suitable mesh sleeve, e.g. by electroforming on a mandrel.

Another form of additional structure which can be positioned over the balloon to provide an outer surface structure that is particularly configured to localise outward force of the balloon as generated by the pressure impulses to only a portion of the balloon surface is now described with reference to FIGS. 4 and 5.

Figure 4:
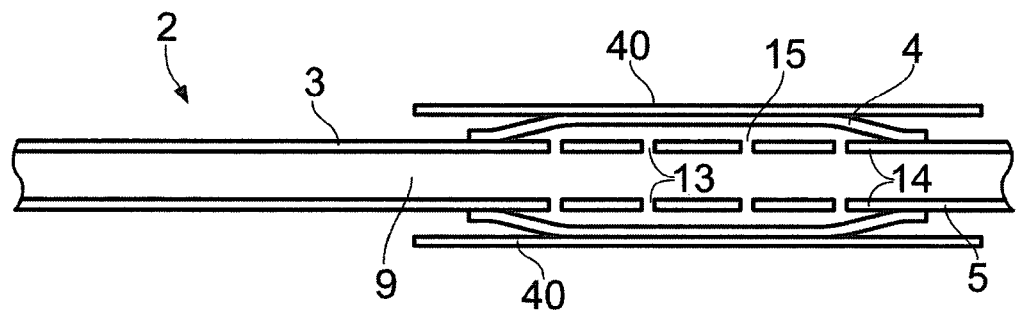
FIG. 4 shows a schematic cross-sectional diagram of a part of a balloon catheter having an alternative type of outer structure configured to provide localised, radially outward force on inflation of the balloon.

With reference to FIG. 4, the distal end 5 of the catheter 3 has the balloon 4 disposed over a series of holes 13 in the wall 14 of catheter lumen 9 for delivery of the pressurization medium such as saline to the internal volume 15 of the balloon 4, as previously discussed with reference to FIG. 2.

The balloon 4 further includes a cylindrical sleeve 40 (best seen in the perspective view of FIG. 5a) comprising a plurality of axially extending elements 41 coupled at each end by circumferential portions 42, 43 and otherwise separated by a plurality of axially extending slits 44. Preferably, the cylindrical sleeve 40 is microfabricated from metal or other relatively hard material so that the individual elements 41 are relatively incompressible, though the overall mesh cylindrical sleeve 40 itself can be flexibly distorted as will be described with reference to FIG. 5b. An exemplary material for the sleeve 40 would be Nitinol or other superelastic alloy.

Figure 5A:
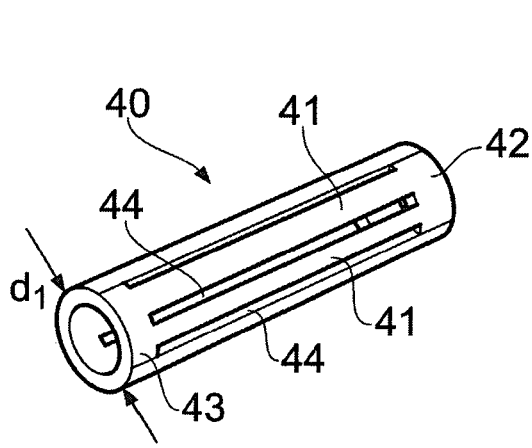
FIG. 5 shows a schematic perspective view of the balloon outer structure of FIG. 4 in an initial configuration for delivery (FIG. 5a) and in an expanded deployed configuration (FIG. 5b)

The sleeve 40 is preferably configured such that it has a first diameter d1 as seen in FIG. 5a which corresponds to the diameter of the circumferential portions 42, 43. The first diameter preferably corresponds closely with that of the uninflated balloon 4 so that it has little effect on the diameter of the balloon catheter 2 used in the vessel 60 during delivery. In some examples, the balloon may have a collapsed diameter of approximately 0.6 mm and the sleeve 40 may have a diameter of 0.8 mm with wall thickness (for the elements 41 and circumferential portions 42, 43) of 120 microns.

Figure 5B:
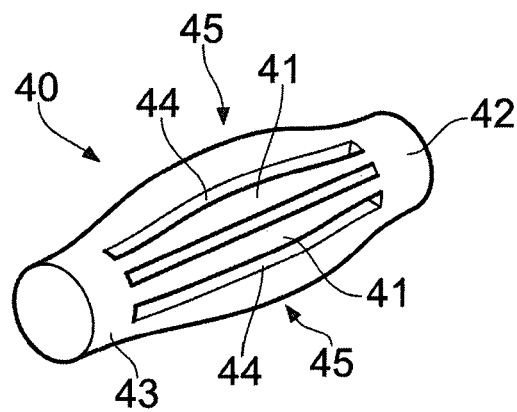

With reference to FIG. 5b, upon inflation of the balloon 4, the sleeve 40 is distorted by the expanding balloon such that the axially extending elements 41 are displaced radially outward creating an expansion apex 45 generally towards the midpoint along the sleeve axis. The radial displacement of the axially extending elements 41 can be achieved by a small shortening along the axis of the device, and the circumferential portions 42, 43 can displace axially towards one another to achieve this.

In this way, the elements 41 of the sleeve 40 will expand radially outwards with the balloon when the balloon is inflated in situ, to bear against any deposits 61. There may be particular focus at apexes 45. Thus, each element 41 may provide a localised hard surface which is used as a hammer surface against the deposits 61 when the balloon surface is displaced by the pressure impulses from the pressure modulation source 12.

The number and geometry of slits 44 provided around the circumference of the sleeve 40 can be varied according to optimal performance. The axially extending slits need not be straight, and they could extend at least partially around the circumference of the sleeve so that the axially extending elements have a helical form, for example. Other geometric shapes and patterns are possible. The axially extending elements 41 may include localised pressure points, such as nodules or bumps on the outer surfaces thereof for further localising the outward force of the pressure impulses. The sleeve 40 may be fixed to the catheter at one or both ends.

Figure 6B:
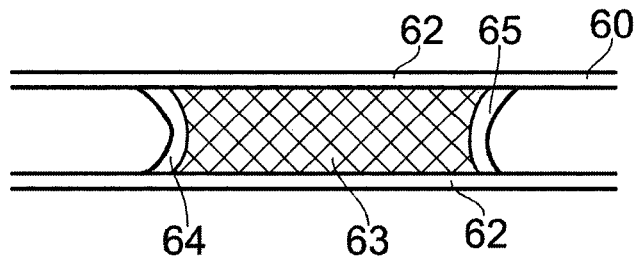
FIG. 6b represents a state of total occlusion with hardened axial ends shown as proximal and distal caps.

With reference to FIG. 6b, another form of calcification that can occur is chronic total occlusion, in which the deposits 63 completely or substantially completely occlude the vessel 60. In such a condition, the calcified deposits 63 may include proximal and/or distal caps 64, 65 comprising regions of heavy calcification which cannot readily be penetrated by a guidewire being used to guide the balloon catheter to the treatment site. In such a circumstance, a complex procedure of attempting to force the guidewire between the vessel wall 62 and the outside of the plug 63 may conventionally be attempted. This can be a difficult manoeuvre to make and may involve increased risk of damage to the vessel 60.

Figure 7:
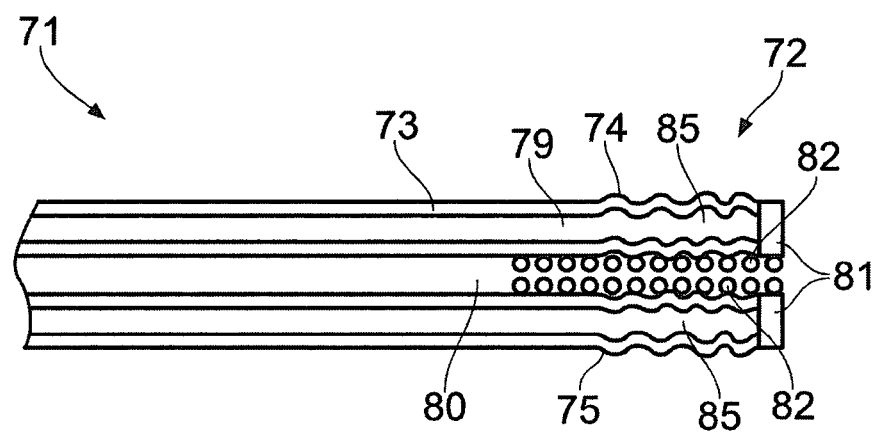
FIG. 7 shows a schematic cross-sectional view of a part of a balloon catheter having an axially displaceable end structure configured to provide localised, axial force upon inflation of the balloon.

With reference to FIG. 7, an alternative configuration of balloon catheter 72 in a medical device 71 uses the pressure modulation system 12 described in connection with FIG. 1 which can be deployed to assist in the break-up, disruption or disintegration of the calcified material 63 or other hardened material forming a plug, including in particular the proximal cap 64 of FIG. 6b.

As shown in FIG. 7, the distal end 75 of the catheter 73 has a balloon 74 in communication with a catheter outer lumen 79 for delivery of the pressurization medium such as saline to an internal volume 85 of the balloon 74. The lumen 79 is an outer lumen, with the catheter 73 having an inner lumen 80 through which a guidewire (not shown) may pass in known manner, so that the balloon catheter 72 can be introduced into the vessel 60 over the guidewire up to the point where it is blocked by the proximal cap 64 (FIG. 6b).

In this arrangement, however, rather than being configured for radial expansion, the balloon 74 is configured for axial expansion from the distal end 75 of the catheter. The balloon 74 may take the form of a corrugated cylinder, e.g. with a 'concertina-fold' type chamber as shown in FIG. 7, or other type of bellows or bellows-like structure. The expression "balloon" in this context is intended to encompass other such bellows-type structures and other flexible fluid chambers, expandable under inflation pressure. This provides for axial displacement of an end surface of the balloon. The balloon 74 could also be adapted for radial expansion for stability within the vessel 60 or this could be achieved with a separate balloon, if required, e.g. in a more proximal position along the catheter 73. At the distal end of the balloon 74 is preferably disposed an outer surface structure in the form of a hard element 81 suitable for focussing the pressure impulse energy from the pressure modulation source 12 into a localised region. This hard element 81 could comprise one or more weights or a collar with ribs or nodules or axially extending nodes or other protuberances giving one or more focal points on the axial end of the balloon catheter 72, suitable for focussing pressure impulses.

The distal end 75 of the catheter 72 may include a spring element 82 to assist in a return bias to the axial balloon expansion when the pressure modulation generated by the pressure modulation source 12 is zero, i.e. when the pressure in the outer lumen 79 is at the baseline pressure provided by the pump 11 or provided by ambient pressure.

The time varying pressure component provided by the pressure modulation source 12 can thereby cause the hard element 81 to vibrate and act as a micro-impact percussion hammer. This assists in break up or disintegration of the deposits 63 and in particular any hardened proximal cap 64.

The structure as shown in FIG. 7 could be implemented in numerous different ways. For example, the hard element 81 could be driven by a balloon disposed within an end of the catheter lumen and extending from the end thereof, or the balloon could be disposed entirely within the catheter lumen and the hard element could extend into the lumen to the balloon component by a link member to be driven thereby. In this context, the balloon may comprise any expandable member inside or outside the catheter 73 and capable of providing an axial displacement under the control of the pressure modulation source at the proximal end of the catheter. The hard element 81 could be driven by a piston or diaphragm in communication with the pressurized lumen of the catheter. The piston or diaphragm could be biased by a spring against the pressurizing medium in the catheter lumen.

Figure 8:
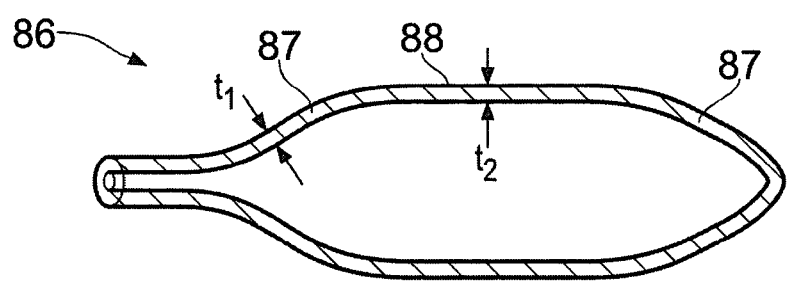
FIG. 8 shows a schematic longitudinal cross-sectional view of a balloon for a balloon catheter.

Another possible configuration of balloon for a balloon catheter is shown in FIG. 8, which shows a balloon 86 having thicker walls (e.g. thickness $t_1$) at the axial end portions 87 and thinner walls (e.g. thickness $t_2$) at the axially central portion 88. This arrangement may assist in providing greater radial displacement in the central portion 88 under the action of the pressure impulses, while providing greater stiffness of the balloon 86 at the axial end portions 87 so as to reduce radial displacement thereby even more effectively transferring energy from the pressure modulation source 12 to the central portion 87. It will be understood that this balloon 86 could be used in conjunction with balloon catheters generally as described herein, e.g. with the mesh sleeve 20 and the cylindrical sleeve 40.

Figure 9:
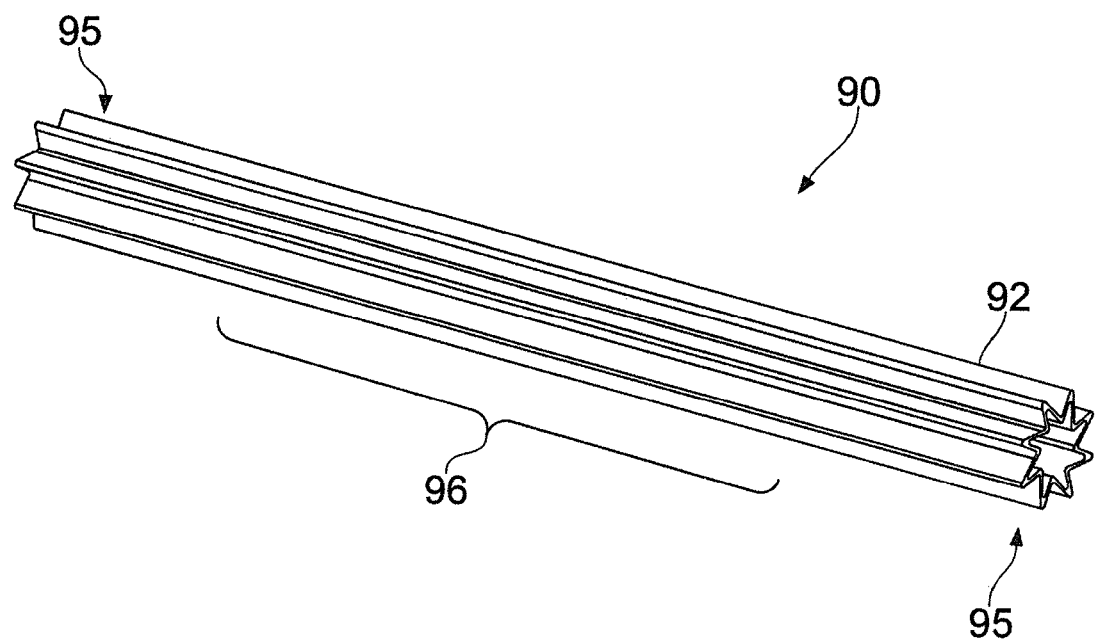
FIG. 9 shows a perspective view of a part of a balloon or an expandable structure for a balloon catheter.
Figure 10:
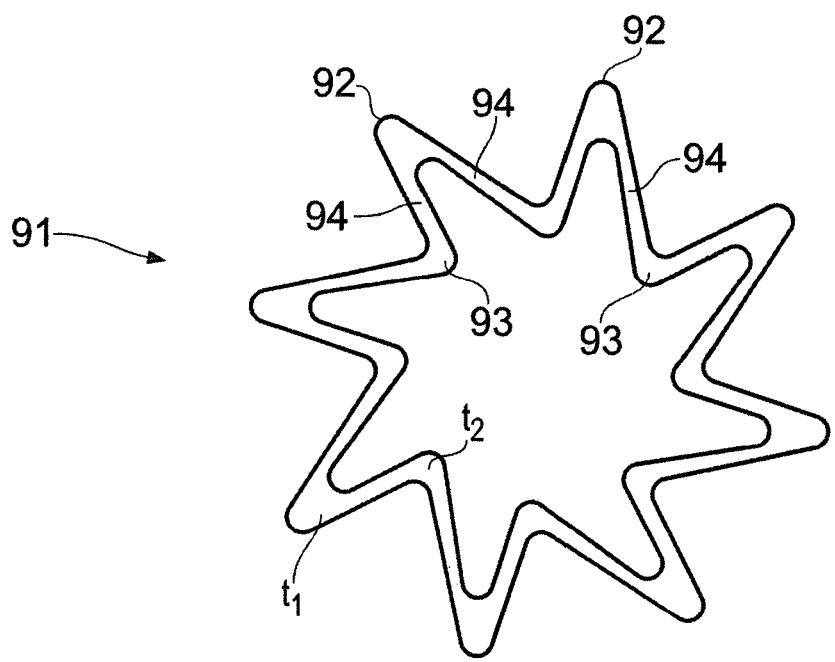
FIG. 10 shows a schematic lateral cross-sectional view of the balloon or expandable structure of FIG. 9.

Another possible configuration of balloon catheter is shown in FIGS. 9 and 10. In this arrangement, the expandable structure or balloon 90 can be formed using a foldable metal structure. In the example shown, the expandable structure has a star configuration lateral cross-section 91 comprising a plurality of radial maxima 92 (e.g. folds) and a plurality of radial minima 93 (e.g. folds) with radial transition portions 94 between. In the example of FIGS. 9 and 10 it can be seen that the radial transition portions 94 are substantially straight and the radial maxima and minima are substantially triangular, to give the star-shaped cross-sectional profile. However, it will be understood that the radial maxima 92 and/or radial minima 93 and/or radial transition portions 94 could be more generally curved to form the localised radial maxima and minima. However, a preferred profile, as shown, provides relatively pointed radial maxima 92 as nodes to provide small, focussed points or lines of hard and sharp surface to serve as hammer surfaces against deposits 61 (FIG. 6a). The expandable structure 90 can serve as a balloon with the ends closed and coupled to the catheter 3. Alternatively the expandable structure 90 may serve as an additional structure or sleeve which is positioned over a balloon 4 in a similar manner to that described in connection with FIGS. 2 to 4.

The wall thickness of the balloon/expandable structure 90 can be variable. In the example shown, the wall thickness $t_1$ at the radial maxima is greater than the wall thickness $t_2$ at the radial minima and radial transition portions. This improves the transfer of impulse energy to the deposits 61 by the nodes of the radial maxima, and allows greater flexibility to the radial minima and radial transition portions so that they can be readily deflected to enable inflation of the balloon 90 and also to enable transient radial displacement of the radial maxima by the pressure modulation source 12. Further hardening features could be formed on the surface of the radial maxima folds to maximise the force transmission to the deposits 61.

If the balloon/expandable structure 90 is formed of metal, since metals are not generally stretchable, the metal structure can be electroformed to minimise generation of high local stresses within the metal during expansion, to avoid risk of rupture. The variation in thickness of the material of the balloon 90 can also vary along the axial length of the balloon, for example providing a gradual increase in metal thickness towards the axial ends 95 of the balloon and a decrease towards the central region 96. The thickness could vary axially in a similar fashion to that showing in the balloon of FIG. 8. The overall diameter of the balloon may also vary along the axial length of the balloon, e.g. with a decrease in diameter towards the axial ends 95.

Figure 11:
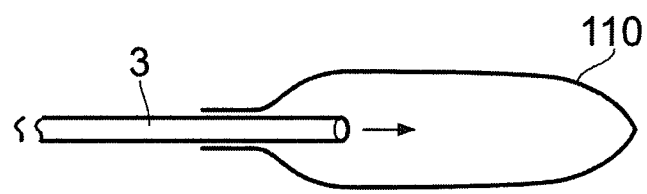
FIG. 11 shows a schematic longitudinal cross-sectional view of a balloon catheter.
Figure 12:
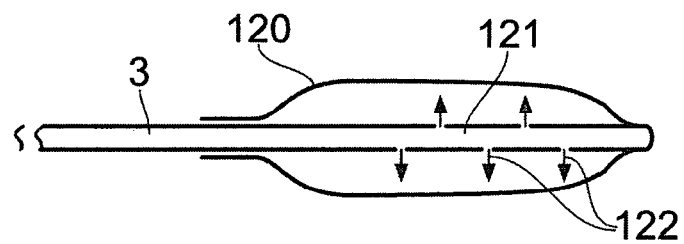
FIG. 12 shows a schematic longitudinal cross-sectional view of a balloon catheter for filling to create cavitation bubbles.

In other modifications, the way the catheter tube 3 enters the balloon or expandable structure 4 can be changed. In one embodiment as seen in FIG. 11, the catheter tube 3 can be directly coupled to the balloon/expandable structure 110 to enable filling the balloon directly. In another embodiment 120 seen in FIG. 12, the catheter tube 3 can be connected to or include a closed ended or blind tube 121 extending axially through the balloon 120 with apertures 122 (e.g. holes or slots) on the outer (circumferential) surface of the tube 121. These apertures 122 may be configured such that, under high fluid flow rates through the apertures, areas of low/high local pressure result in cavitation bubbles that exert high impact upon their collapse.

In general, the catheter devices as described above may have one or more suitable displaceable elements at the distal end of catheter, which may each be axially and/or radially displaceable, each of which may be driven separately or in concert by a pressure pump at the proximal end of the catheter with a pressure modulation source, to create pressure impulses on the displaceable element or elements. One or more lumens in the catheter may be used to displace the one or more displaceable elements.

Resonance

The devices described above may be further modified to exploit resonant behaviour of the balloon 4 and the outer surface structure (e.g. 20, 40, 81 or 90) so as to increase or maximise displacement of the outer surface or outer surface structure of the balloon. Thus, the frequency of the waveform of pressure modulation provided by the pressure modulation source 12 may be selected according to obtaining optimal displacement of the balloon 4 and/or outer surface structure 20, 40, 81, 90. This may also take into account the effect of the calcified deposits or other deposits 61, 63 on the resonant frequency. This may also take into account the effect of the vessel structure 60 on the resonant frequency.

The pressure modulation source 12 may be provided with sensing capability to sense the impedance of the system under deployment within the vessel in order to automatically select and/or track a modulation frequency that optimises the displacement of the balloon and/or outer surface structure. The pressure modulation source may be configured to scan through an appropriate frequency spectrum to determine the optimum modulation frequency, for example to cause maximum displacement to the calcified deposits 61 for minimum energy input. The pressure modulation source may alternatively or additionally be configured to determine an optimum modulation frequency to cause maximum force to the calcified deposits 61. The pressure modulation source may operate to determine anti-resonance or resonance conditions, and may switch between them for optimal impact.

The sleeve 40 may be modified in its resonance performance, e.g. by customising the slit 44 widths and lengths, or the element 41 widths and lengths, and modifying the thickness and type of material used. The spring element 82 in the device of FIG. 7 could also be used to tune for a particular resonance performance.

Catheter

The catheter 3 may be of any suitable type and may include a metal or rigid tube with a non-distensible but steerable part that can be metal or polymer reinforced with metal coiling. The steerable part may be terminated with the balloon expandable parts as described above.

The balloon catheter device as described above enables endovascular therapy at controlled depth and energy to enable localised disruption of vascular calcium (analogous to the spiders-web fracturing of a car windscreen) facilitating subsequent PCI. By locally fracturing calcium deposits it would increase vascular compliance, enabling traditional PCI approaches of balloon dilation and stenting to be safely employed using standard techniques. The device could be adapt to the technology for peripheral vascular disease and for the favourable modification of the proximal calcified cap in chronic total occlusion PCI. The procedure can be guided using conventional fluoroscopy techniques.

An advantage of the described arrangements of a pressure modulated balloon catheter is that the procedure for use is very similar to procedures for use of existing angioplasty balloon catheters and thus the clinical skills in deployment of a conventional balloon catheter for angioplasty procedures and stent implantation are highly relevant to the novel arrangements described here.

The use of the pressure modulation balloon catheters described above can be integrated with existing procedures, e.g. for implantation of stents. After destruction or displacement of the deposits 61, the pressure modulated balloon catheter may be easily withdrawn over the guidewire and the same guidewire then used to deliver a stent. Depending upon the nature of the stent to be deployed, it is possible that the stent for delivery itself may be of an expanding type that can also be used as the additional outer surface structure of the pressure modulated balloon used to focus the energy of the pressure impulses. This would thereby potentially enable the calcium deposit disintegration procedure and the stent deployment to be effected in a single catheter insertion process.

The apparatus can also be used in the placement of non-metallic stents such a bioabsorbable scaffolds, drug-eluting stents or the placement of other drug delivery platforms or the like, into any part of the vasculature.

The apparatus can generally be used in other non-vascular applications. For example, passing the catheter systems described above through the ureter to disrupt kidney stones or through the common bile duct to disrupt gall stones can be envisaged, e.g. where percutaneous lithotripsy cannot be used.

The balloons used in the devices described above may be non-compliant, semi-compliant or compliant balloons depending on the requirement. The catheter material preferably has a high degree of non-compliance or inelasticity for optimal transfer of pressure and pressure modulation to the balloon. A coiled catheter insert may be used for support and steerability according to known techniques.

Throughout the specification, references to a 'proximal end' of the catheter and a 'distal end' of the catheter are intended to also encompass positions towards the respective ends of the catheter. The expression 'at the proximal end' may include a position on the catheter generally intended for use outside the body and the expression 'at the distal end' may generally include a position on the catheter intended for use inside the body at a treatment site within the body.

Pressure Modulation Source

The pressure modulation source 12 may be, for example, a diaphragm displaceable by an electromagnetic actuator driving, for example, a plunger or a bellows. The diaphragm could be periodically displaced by a motor-driven cam or plunger. Simple and more complex waveforms for pressure modulation could readily also be provided by a pressure modulation source comprising an acoustic transducer or ultrasonic transducer, a piezo-electric actuator or a stepper motor driven diaphragm, e.g. for single transient pulses as well as periodic or aperiodic waveforms. The pressure modulation source may comprise an actuator driven pneumatically or hydraulically. Although shown as separate entities in FIG. 1, the pressure modulation source could be combined or integrated with the pump or other pressurization source for providing the baseline pressure.

In a demonstration system a pressure control apparatus 10 was used with a conventional angioplasty balloon. The catheter was filled with saline and a baseline pressure of 2 bars was applied to expand the balloon that was inserted into a simulated calcification. Silicone tubes with a cylindrical layer of cement and plaster were used for initial tests. A baseline pressure of 2 bars was applied. Even without the metal sleeves as proposed above, the pulsating pressure (up to 100 Hz) was able to crack the hard walls of the softer sample of simulated calcification. The system was able to transmit the pulsating pressure through the saline in the catheter into the balloon.

Results

Artificial calcification in rubber tubes of similar diameter to coronary artery was made and used as test material to assess the performance of the system. Successful disruption of calcified material has been consistently confirmed. In two experimental prototypes, the baseline pressure was established by a glass syringe whose piston was advanced by a screw capable of producing baseline pressures up to 20 bars, but a baseline pressure of 2-4 bar is typically used. The first system uses a miniature chamber equipped with a diaphragm driven by a magnetic plunger for impulse pressure generation up to a frequency of 1 kHz. The impact energy of this machine is fixed but the impact frequency is variable. The second system uses a compressed spring-mass energy storage mechanism (similar to impact hammer systems) for pressure impulse generation up to a frequency of 50 Hz. The impact energy of this system is adjustable. The weights on this second system are interchangeable up to 500 grammes, allowing the generation of different impact energies. The control parameter used on the first system is the impulse frequency as the impulse energy is fixed, whereas the second system may be configured to generate a range of impact energies and variable impulse frequency. This second system operates at a lower frequency and can produce higher impacts. This second system allows study of the effect of different parameters as the impulse is easily calculated by the spring constant and weight used. The impact to impulse pressure is performed by a rigid piston mechanism. Three pistons of different diameters were fabricated. The combination of these parameters can be used to produce a wide range of pressure impulses. Although this system is bulkier (28×29×25 cm), it is very effective at disrupting simulated calcification in silicone tubing.

To increase the impact energy transfer to the hard calcification, an expandable metal sleeve 40 was designed, fabricated and coupled to the balloon section of the catheter, similar to that shown in FIG. 5. A finite element model was simulated in COMSOL to study the behaviour of the expandable part under static and pulsed pressure. A suitable number of axially extending slits 44 was identified for easy expansion. To study the resonance behaviour of the part, a time domain analysis was performed and the frequency of resonance was calculated from a step response.

The frequency of resonance was estimated at 5333 Hz to determine the possible driving mechanisms. These calculations suggest that a resonant mode expandable sleeve 40 is feasible. Sleeves 40 of different length and axially extending slits 44 were fabricated by laser cutting Nitinol tubes, including a sleeve of 12 mm length with 16 slits.

These sleeves were tested with the impulse generating unit and it was shown that disruption of simulated calcification in rubber tubes is feasible. A simulated calcified silicone tube was fractured in ~30 seconds under a baseline pressure of 5 bar and an impulse frequency of 25 Hz Another component that is used in conjunction with the impulse pressure generating units is the catheter (with diameter similar to angioplasty catheters) with an expandable section at its distal end. This catheter forms an efficient transmission line for the pressure impulse and consists of a longer metal tube and a reinforced plastic tube. The plastic tube section has two characteristics: 1. Steerability for easy and safe positioning of the catheter tip within the calcified region of the artery and 2. Radial stiffness to ensure that impulses are transmitted without significant distortion. The amplitude of an impulse pressure that travels through a fine tube will naturally be attenuated. This type of damping (resistive loss) can be compensated by generating a high enough initial amplitude. Distortion of an impulse can happen if there is an energy storing element within the transmission line. For example, if a section of the catheter tube is expandable, it can store energy by elastic expansion. This should preferably be avoided for optimal operation of the system, as it widens the impulse width causing a decrease in the impulse force.

Optimum characteristics can be achieved by using a plastic tube reinforced by metal wire coiling. The coiling prevents expansion of the plastic tube in radial direction and ensures that it will not store the impulse energy by expansion, while still allowing flexibility of the tube. As a result, the generated impulse wave can travel in the incompressible fluid without significant loss of the impulse width.

Figure 13:
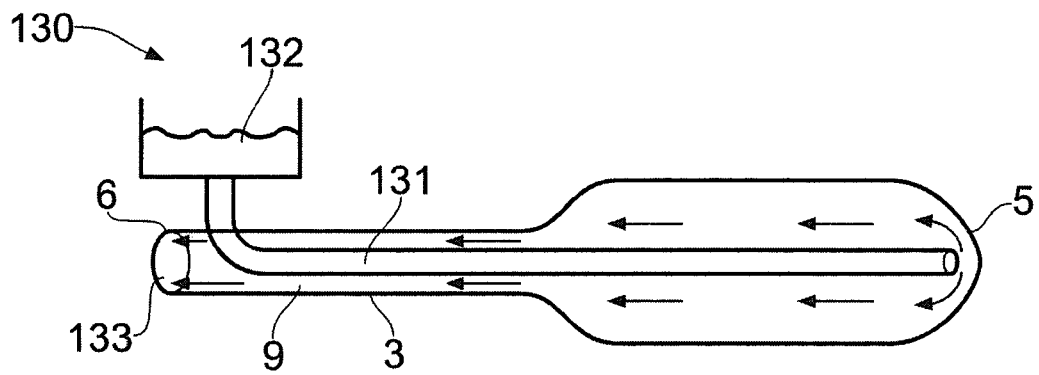
FIG. 13 shows schematic longitudinal cross-sectional diagram illustrating a filling mechanism for the balloon catheter.

It may be desirable to avoid air or other gas bubbles within the transmission medium (incompressible fluid). Any air bubbles within the catheter 3 could act as a (compressible) cushion that will distort the impulse amplitude and more importantly the impulse width. To overcome this problem, as shown in FIG. 13, a catheter filling mechanism 130 may be provided which comprises a fine tube 131 that runs inside and along the lumen 9 of the main catheter 3. This inner tube 131 may extend to the distal end 5 of the device and is connected to liquid reservoir 132. A vacuum 133 is applied to the proximal end 6 of the catheter 3, and liquid is drawn through the inner tube 131 and fills the catheter 3 from its distal end to its proximal end 6. The inner surface of the catheter 3 may be functionalised with a hydrophobic layer, which further reduces the likelihood of formation of trapped air bubbles.

Other embodiments are intentionally within the scope of the accompanying claims.

The invention claimed is:

1. A medical device comprising:
   a catheter having a lumen extending between a distal end and a proximal end of the catheter;
   a displaceable element at the distal end of the catheter configured for axial and/or radial displacement relative to the catheter when driven by pressure fluctuations within the lumen;
   a pressure pump coupled to a proximal end of the catheter and configured for application of a static baseline pressure of up to 20 bars to the catheter lumen so as to provide an incompressible fluid medium in the displacement element that is ready to receive a series of high pressure impulses; and
   a pressure modulation source, coupled to the proximal end of the catheter, configured to modulate the static baseline pressure in the catheter lumen with the series of high pressure impulses with a waveform having a frequency greater than 5 Hz to deliver percussive shock forces to the displaceable element,
   wherein the displaceable element comprises a balloon having an outer surface layer or structure configured to localize outward force of the balloon generated by the high pressure impulses to only a portion of an external surface of the balloon so as to effect by direct contact the break-up, disruption or disintegration of calcified material or other hardened material within vessels of a human or animal body.

2. The medical device of claim 1 in which the pressure modulation source comprises a diaphragm displaceable by an electromagnetic actuator.

3. The medical device of claim 2 in which the electromagnetic actuator comprises a plunger or a cam driven by a motor.

4. The medical device of claim 3 in which the motor comprises a stepper motor.

5. The medical device of claim 1 in which the pressure modulation source comprises an acoustic transducer.

6. The medical device of claim 1 in which the balloon outer surface layer or structure comprises a sleeve having a plurality of axially extending elements which are radially displaceable by balloon expansion.

7. The medical device of claim 6, wherein the sleeve is microfabricated from metal.

8. The medical device of claim 6, wherein the sleeve comprises a network of wires or other link members.

9. The medical device of claim 8, wherein weights or nodules are affixed to or formed on the wires or other link members.

10. The medical device of claim 1 in which the pressure modulation source is configured to modulate the static baseline pressure with a waveform having a frequency greater than 10 Hz or greater than 100 Hz.

11. The medical device of claim 1 in which the pressure modulation source is configured to vary a frequency of modulation of the static baseline pressure to a resonant frequency of the balloon and any outer surface structure of the balloon.

12. The medical device of claim 1, wherein the pressure modulation source comprises a sensing capability configured to sense an impedance of the displaceable element under deployment within a vessel of the human or animal body, wherein the pressure modulation source is further configured to select and/or track a modulation frequency based on the sensed impedance so as to cause, by the balloon:
    maximum displacement of the calcified material or other hardened material for a minimum energy input, or
    maximum force to the calcified material or other hardened material.

13. The medical device of claim 12, wherein the pressure modulation source is further configured to scan through a frequency spectrum to determine the modulation frequency.

* * * * *